United States Patent
Raksi et al.

(10) Patent No.: US 8,292,877 B2
(45) Date of Patent: Oct. 23, 2012

(54) SYSTEM AND METHOD FOR INCISING MATERIAL

(75) Inventors: Ferenc Raksi, Irvine, CA (US); Michael Brownell, San Clemente, CA (US)

(73) Assignee: AMO Development, LLC., Santa Ana, CA (US)

( * ) Notice: Subject to any disclaimer, the term of this patent is extended or adjusted under 35 U.S.C. 154(b) by 0 days.

(21) Appl. No.: 13/400,345

(22) Filed: Feb. 20, 2012

(65) Prior Publication Data

US 2012/0150161 A1    Jun. 14, 2012

Related U.S. Application Data

(62) Division of application No. 11/936,635, filed on Nov. 7, 2007, now Pat. No. 8,142,423.

(51) Int. Cl.
*A61F 9/01* (2006.01)
(52) U.S. Cl. .................................. 606/4; 606/5; 152/898
(58) Field of Classification Search .................. 606/4, 5; 128/898
See application file for complete search history.

(56) References Cited

U.S. PATENT DOCUMENTS

| | | | |
|---|---|---|---|
| 4,764,930 A | 8/1988 | Bille et al. | |
| 4,901,718 A | 2/1990 | Bille et al. | |
| 5,019,097 A * | 5/1991 | Knight et al. | 623/5.13 |
| 5,520,679 A | 5/1996 | Lin | |
| 5,599,340 A | 2/1997 | Simon et al. | |
| 5,800,424 A | 9/1998 | Sumiya | |
| 5,993,438 A | 11/1999 | Juhasz et al. | |
| 6,110,166 A | 8/2000 | Juhasz | |
| 6,325,792 B1 | 12/2001 | Swinger et al. | |
| RE37,585 E | 3/2002 | Mourou et al. | |
| 6,451,006 B1 | 9/2002 | Bille | |
| 6,641,577 B2 | 11/2003 | Bille | |
| 6,805,694 B2 * | 10/2004 | Donitzky | 606/5 |
| 7,131,968 B2 | 11/2006 | Bendett et al. | |
| 7,211,077 B1 | 5/2007 | Rampona | |
| 2001/0010003 A1 | 7/2001 | Lai | |

(Continued)

FOREIGN PATENT DOCUMENTS

EP    1473006 A1    11/2004

(Continued)

OTHER PUBLICATIONS

International Preliminary Report on Patentability and Written Opinion for Application No. PCT/US08/082716, mailed on May 11, 2010, 9 pages.

(Continued)

*Primary Examiner* — Ahmed M Farah
*Assistant Examiner* — Jeffrey Lipitz
(74) *Attorney, Agent, or Firm* — AMO Development, LLC.

(57) ABSTRACT

Systems and methods of incising a portion of a material include creating a sub-surface separation in a region of the material, and incising a periphery of the region with a pulsed laser beam to produce an edge of the portion. The edge includes a periodically varying shape to secure the portion to the material when the portion is reintegrated. The system includes a laser producing the pulsed laser beam, a scanner operable in response to a control signal, and a controller coupled to the scanner. The controller produces the control signal. In response to the control signal, the scanner creates a sub-surface separation in the region with the pulsed laser beam and incises the periphery of the region with the pulsed laser beam to produce the edge with the periodically varying shape.

14 Claims, 4 Drawing Sheets

U.S. PATENT DOCUMENTS

| | | |
|---|---|---|
| 2001/0016736 A1 | 8/2001 | Lin |
| 2001/0037105 A1 | 11/2001 | Lin |
| 2002/0173779 A1* | 11/2002 | Donitzky .................... 606/5 |
| 2003/0100893 A1 | 5/2003 | Bille |
| 2003/0132208 A1 | 7/2003 | Cutler |
| 2003/0208189 A1 | 11/2003 | Payman |
| 2003/0212387 A1* | 11/2003 | Kurtz et al. ................. 606/4 |
| 2004/0199150 A1 | 10/2004 | Lai |
| 2004/0209410 A1 | 10/2004 | Tanaka |
| 2004/0243111 A1 | 12/2004 | Bendett et al. |
| 2004/0243112 A1 | 12/2004 | Bendett et al. |
| 2005/0245915 A1 | 11/2005 | Loesel et al. |
| 2006/0027544 A1 | 2/2006 | Pailthorp et al. |
| 2006/0155265 A1* | 7/2006 | Juhasz et al. ................ 606/5 |
| 2006/0195076 A1 | 8/2006 | Blumenkranz et al. |
| 2007/0088409 A1 | 4/2007 | Bischoff et al. |
| 2007/0179479 A1 | 8/2007 | Bille |
| 2007/0235543 A1 | 10/2007 | Zadoyan et al. |
| 2008/0051769 A1 | 2/2008 | Mrochen et al. |
| 2009/0118716 A1 | 5/2009 | Brownell |
| 2009/0118718 A1 | 5/2009 | Raksi et al. |

FOREIGN PATENT DOCUMENTS

| | | |
|---|---|---|
| EP | 1591087 A1 | 11/2005 |
| EP | 1731120 A1 | 12/2006 |
| EP | 1834615 A1 | 9/2007 |
| WO | WO9717903 A1 | 5/1997 |
| WO | WO2004003625 A | 1/2004 |
| WO | WO2004017878 A | 3/2004 |
| WO | WO2005058216 A | 6/2005 |

OTHER PUBLICATIONS

International Search Report for Application No. PCT/US08/082716, mailed on Mar. 10, 2009, 4 pages.

* cited by examiner

SYSTEM AND METHOD FOR INCISING MATERIAL

CROSS-REFERENCES TO RELATED APPLICATIONS

The present application claims priority to and is a divisional application of U.S. patent application Ser. No. 11/936,635 filed on Nov. 7, 2007, of which is hereby incorporated by reference in its entirety.

BACKGROUND OF THE INVENTION

1. Field of the Invention

The field of the present invention is generally related to photoalteration of materials and more particularly, to systems and methods for incising a portion of a material.

2. Background

Reshaping the cornea of an eye can correct various vision impairments such as myopia, hyperopia, astigmatism, or the like. Some procedures for reshaping the cornea utilize laser beams to photoalter a desired area of the eye. Examples of photoalteration include, but are not necessarily limited to, chemical and physical alterations, chemical and physical breakdown, disintegration, ablation, vaporization, or the like. One example of photoalteration using pulsed laser beams is the photodisruption (e.g., via laser induced optical breakdown) of corneal tissue. Localized photodisruptions can be placed at the surface of the cornea or sub-surface. For example, a micro-optics scanning system may be used to scan pulsed laser beams to produce an incision in the cornea and create a flap therefrom. The term "scan" or "scanning" refers to the movement of the focal point of a pulsed laser beam along a desired path. To create a flap, the pulsed laser beam is typically scanned along a pre-determined region (e.g., within the corneal tissue) in either a spiral pattern or a raster pattern. A sidecut is subsequently made that encircles most of the scanned region while leaving a portion intact to form a hinge for the flap.

The biomechanical integrity of the cornea may be reduced after performing flap-based or incision-based procedures. In some cases, flap incisions are utilized that ease the separation of the flap from the underlying corneal bed. These flap incisions generally produce a smooth or "clean" tissue separation that reduces the biomechanical integrity of the cornea when the flap is reintegrated (e.g., typically by returning the flap into the underlying corneal bed) with the cornea post-procedure. Additionally, the resulting flap can be inadvertently displaced, and repositioning the flap can affect the visual outcomes. These conventional flap incisions or the displacement of the flap can affect healing of the treated corneal tissue.

Accordingly, it is desirable to provide systems and methods for creating a flap of material that improve the biomechanical integrity of material with the flap reintegrated therewith. More particularly, it is desirable to provide systems and method for creating corneal flaps that improve the biomechanical integrity of the cornea and/or promote healing of the cornea following reintegration of the flap with the cornea. It is also desirable to provide systems and method for incising corneal tissue for keratoplasty that improves the biomechanical integrity and/or promotes healing of the cornea with the transplanted corneal tissue. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed towards incising a piece of a material through selective photoalteration of the material. In one embodiment, a method of incising a piece of a material is provided. The method includes creating a sub-surface separation in a region of the material, and incising a periphery of the region with a pulsed laser beam to produce an edge of the piece. The edge has a periodically varying shape configured to secure the piece to the material when the piece is reintegrated with the material.

In another embodiment, a method of incising a piece of a cornea is provided. The method includes creating a sub-surface separation in the cornea, and incising a periphery of a region of the cornea with a pulsed laser beam to produce an edge of the piece. The sub-surface separation includes a lamellar bed in the cornea, and the bed has a first area and a second area contiguous with the first area. The second area is less smooth than the first area.

In another embodiment, a system for incising a piece of a cornea is provided. The system includes a laser operable to produce a pulsed laser beam, a controller operable to produce a control signal, and a scanner coupled to the scanner. The scanner is operable in response to the control signal to create a sub-surface separation in a region of the cornea with the pulsed laser beam, and incise the periphery of the region with the pulsed laser beam to produce an edge of the piece. The edge has a periodically varying shape configured to secure the piece to the cornea when the piece is reintegrated with the cornea.

In yet another embodiment, a system for incising a piece of a cornea is provided including a laser operable to produce a pulsed laser beam, a controller operable to produce a control signal, and a scanner coupled to the controller and operable in response to the control signal to scan a first pattern along a first sub-surface area of the region with the pulsed laser beam, and scan a second pattern along a second sub-surface area of the region with the pulsed laser beam. The second sub-surface area is contiguous with the first sub-surface area. The first sub-surface area and the second sub-surface area together form a bed of the cornea. The second pattern is configured to assist healing of the piece with the bed when the piece is reintegrated with the cornea.

BRIEF DESCRIPTION OF THE DRAWINGS

In the drawings, wherein like reference numerals refer to similar components.

DETAILED DESCRIPTION

The present invention provides systems and methods for incising a portion of a material while improving characteristics of the flap to facilitate reintegration with the material. In one embodiment, corneal flaps may be created for various ophthalmic procedures and thus, these systems and methods are applicable to any of these ophthalmic procedures or to other ophthalmic applications where incisions are utilized (e.g., corneal transplants or the like). In another embodiment, the systems and method may be used to incise and transplant donor corneal tissue to a recipient cornea. Utilizing these systems and methods, a portion of a cornea is created having an edge with properties (e.g., edge shape or geometry, flap texture as implemented during flap creation, or the like) that enhance the healing process of the cornea (i.e., reintegrating the flap with the cornea) following an ophthalmic procedure, for example, and/or enhance the biomechanical integrity of the cornea following the procedure. In general, one or more of pro-active healing incisions, compound patterns, pre-healing textures, or the like, are incorporated during flap creation. For example, femtosecond laser parameters can be controlled to create a stromal surface that is more conducive to healing (e.g., a "stickier" stromal surface in an outer-annular region of the lamellar bed). Compound patterns may be used to implement these stromal surfaces. With this treated stromal surface, relatively large areas of healing are provided between the lamellar bed and flap in the region near the edges and containing Bowmans layer, for example. Although described in relation to corneal tissue, other materials, both organic and inorganic, may also be used with these systems and methods to create a flap.

In general, photoalteration of a material may be accomplished using a pulsed laser beam that is directed (e.g., via a scanner) at a desired region of the material. For example, a pulsed laser beam may be controlled to scan a desired region in the material to produce a flap. To impart at least a portion of this control, software, firmware, or the like, operated by a controller can be used to command the actions and placement of the scanner via a motion control system, such as a closed-loop proportional integral derivative (PID) control system.

Figure 1:
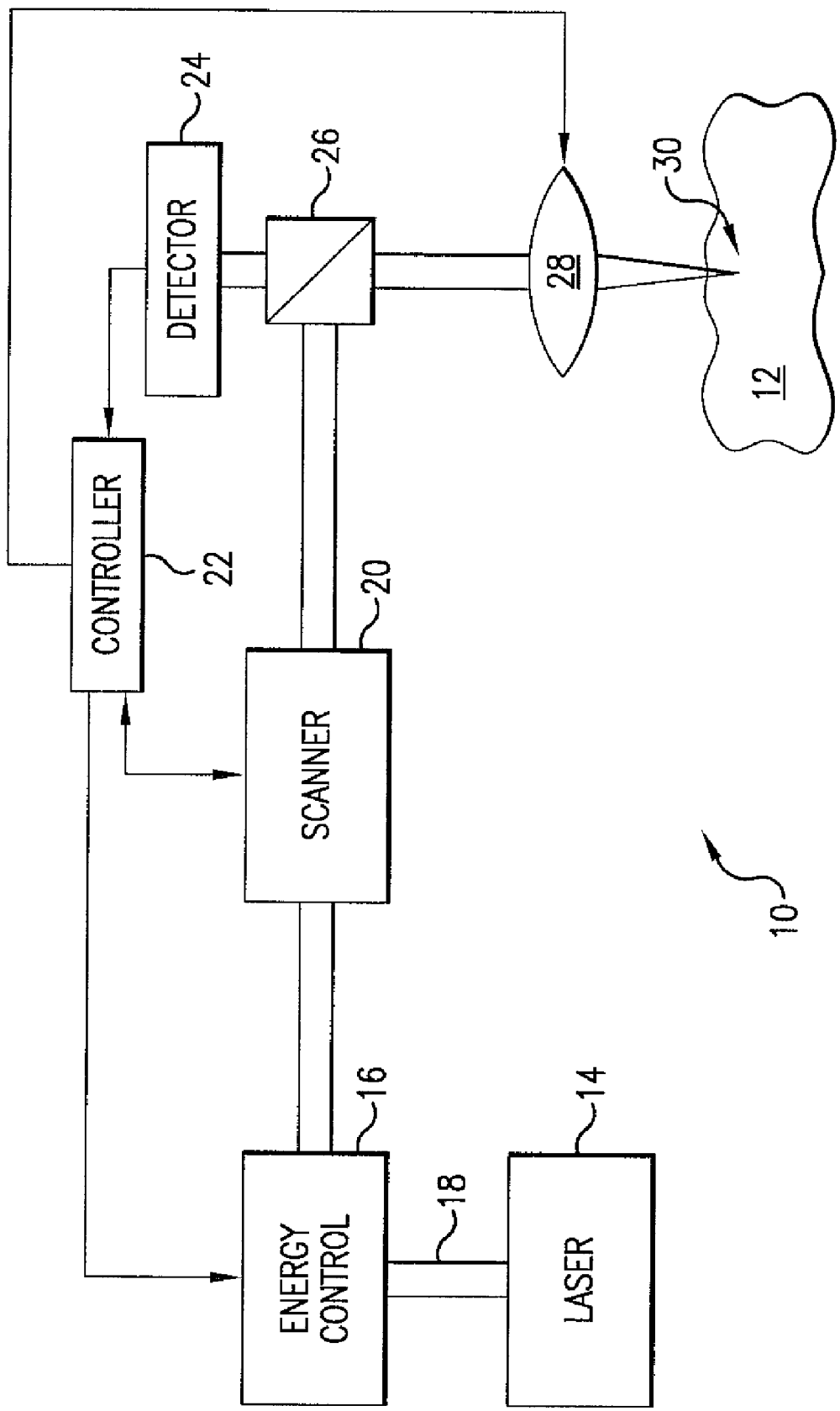
FIG. 1 is a block diagram of a laser scanner system in accordance with one embodiment of the present invention.

Referring to the drawings, a system 10 for photoaltering a material 12 is shown in FIG. 1. The system 10 includes, but is not necessarily limited to, a laser 14 capable of generating a pulsed laser beam 18, an energy control module 16 for varying the pulse energy of the pulsed laser beam 18, a scanner 20 operable in response to a control signal, a controller 22 operable to transmit the control signal, and focusing optics 28 for directing the pulsed laser beam 18 from the laser 14 on or within the material 12. The controller 22, such as a processor operating suitable control software, transmits a control signal to control the scanner 20 and/or focusing optics 28 to direct a focal point 30 of the pulsed laser beam along a scan pattern on the surface of the material or in the material 12 (e.g., at a sub-surface depth). For example, the pulsed laser beam 18 may be scanned at a rate between about 1 kHz and about 1 GHz, with a pulse energy of about 800 nJ/pulse, with a pulse width between about 300 picoseconds and about 10 femtoseconds, and/or at a wavelength between about 400 nm to about 3000 nm. In this embodiment, the system 10 further includes a beam splitter 26 and a detector 24 coupled to the controller 22 for a feedback control mechanism of the pulsed laser beam 18.

The scanner 20 moves the focal point of the pulsed laser beam 18 in increments through a desired scan pattern as controlled by the controller 22. The step rate at which the focal point is moved is referred to herein as the scan rate. For example, the scanner 20 can operate at scan rates between about 10 kHz and about 400 kHz, or at any other desired scan rate, and may selectively switch between one or more substantially constant scan rates. In one embodiment, the scanner 20 generally moves the focal point of the pulsed laser beam 18 through a desired scan pattern at a substantially constant scan rate while maintaining a substantially constant separation between adjacent focal points of the pulsed laser beam 18. For a given scan pattern or combination of scan patterns (e.g., a compound scan pattern), the time for completing the scan pattern is generally inversely proportional to the scan rate. Further details of laser scanners are known in the art, such as described, for example, in U.S. Pat. No. 5,549,632, the entire disclosure of which is incorporated herein by reference.

To provide the pulsed laser beam, a chirped pulse laser amplification system, such as described in U.S. Pat. No. RE 37,585, may be used for photoalteration. U.S. Pat. Publication No. 2004/0243111 also describes other methods of photoalteration. Other devices or systems may also be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

Although the system 10 may be used to photoalter a variety of materials (e.g., organic, inorganic, or a combination thereof), the system 10 is suitable for ophthalmic applications in one embodiment. In this case, the focusing optics 28 direct the pulsed laser beam 18 toward an eye (e.g., onto a cornea) for plasma mediated (e.g., non-UV) photoablation of superficial tissue, or into the stroma for intrastromal photodisruption of tissue. In this embodiment, the system 10 may also include an applanation lens (not shown) to prepare the cornea for scanning by the pulsed laser beam 18. The system 10 is capable of generating the pulsed laser beam 18 with physical characteristics similar to those of the laser beams generated by a laser system disclosed in U.S. Pat. Nos. 4,764,930, 5,993,438, or the like.

For example, the ophthalmic laser system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue except at the focal point depth of the pulse laser beam 18. The wavelength of the pulsed laser beam 18 is generally in the range of about 3 µm to about 1.9 nm, preferably between about 400 nm to about 3000 nm, and the irradiance of the pulsed laser beam 18 for accomplishing photodisruption of stromal tissues at the focal point is greater than the threshold for optical breakdown of the tissue.

Although a non-UV, ultrashort pulsed laser beam is described in this embodiment, the pulsed laser beam 18 may have other pulse durations and different wavelengths in other embodiments.

For ophthalmic applications, the scanner 20 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis. In preparing a corneal bed for flap separation, for example, a circular area may be scanned using a scan pattern driven by the scanning mirrors. The pulsed laser beam 18 photoalters the stromal tissue by scanning the focal point of the pulsed laser beam 18 in a pattern of spots (e.g., based on the scan pattern), the distribution of which is determined by the pulse frequency, the scan rate, and the amount of scan line separation. Generally, higher scan rates, enable shorter procedure times by increasing the rate at which corneal tissue can be photoaltered. For example, the scan rates may be selected from a range between about 30 MHz and about 1 GHz with a pulse width in a range between about 300 picoseconds and about 10 femtoseconds, although other scan rates and pulse widths may be used. While scanning is described using mirrors and focusing objectives to direct the pulsed laser beam in one embodiment, the system 10 may be configured with a moveable laser head to direct the pulsed laser beam at a desired region and along a desired path in another embodiment.

The system 10 may additionally acquire detailed information about optical aberrations to be corrected, at least in part, using the system 10. Examples of such detailed information include, but are not necessarily limited to, the extent of the desired correction, and the location in the cornea of the eye where the correction can be made most effectively. The refractive power of the cornea may be used to indicate corrections. Wavefront analysis techniques, made possible by devices such as a Hartmann-Shack type sensor (not shown), can be used to generate maps of corneal refractive power. Other wavefront analysis techniques and sensors may also be used. The maps of corneal refractive power, or similar refractive power information provided by other means, such as corneal topographs or the like, can then be used to identify and locate the optical aberrations of a cornea that require correction. Additionally, the system 10 may receive data from excimer-based ophthalmic procedures and diagnostics, including wavefront analysis and OCT. For example, OCT data may be used for precision flap depth parameters, excimer nomograms may be used for compound flap parameters, and wavefront analysis may be used to optimize/minimize the effects from creating a flap.

Figure 2:
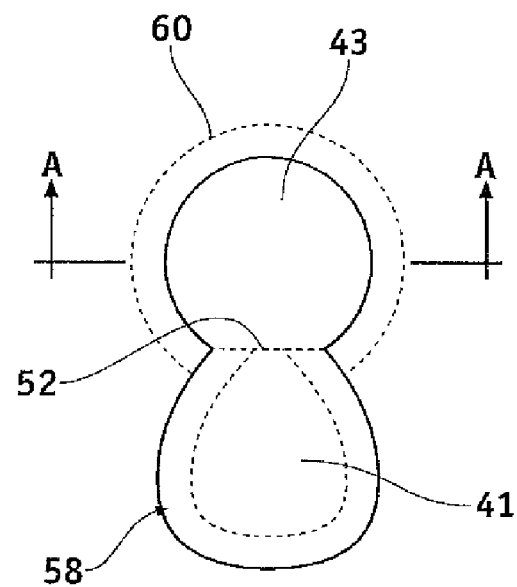
FIG. 2 is a top view of a flap of a cornea and a flap bed in accordance with one embodiment.
Figure 3:
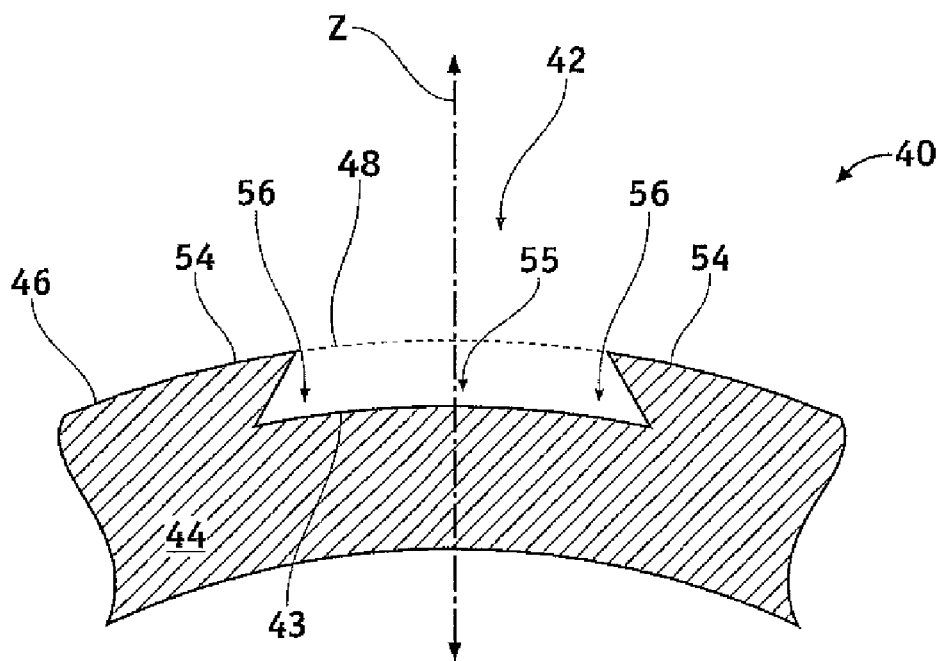
FIG. 3 is a partial sectional view of the cornea shown in FIG. 2 taken along line A-A illustrating a flap incision in accordance with one embodiment.

FIG. 2 is a top view of a flap 41 of a cornea 40 and a flap bed 43 associated with the flap 41 in accordance with one embodiment. FIG. 3 is a partial sectional view of the cornea 40 shown in FIG. 2 taken along line A-A illustrating a flap incision 42. Although the flap 41 is substantially circular, an oval-shaped flap may be used for larger stromal beds and to extend the flap further out of the ablation region for improved matching anatomy. The cornea 40 has an anterior surface 46 and a stromal region 44. The flap incision 42 is formed in the stromal region 44 of the cornea 40 to create the flap 41, although the flap incision 42 may be formed in other regions of the cornea 40 or extend to other regions of the cornea 40 (e.g., Bowman's layer or the like). After incising the flap 41, the flap 41 may be considered to have an exterior surface 48 that is originally a part of the anterior surface 46 of the cornea 40. After re-integrating the flap 41 with the cornea 40, this exterior surface 48 returns to being substantially contiguous with the anterior surface 46 of the cornea 40.

Referring to FIGS. 1 and 2, the system 10 may be used to form the flap 41. Generally, the focal spot 30 of the pulsed laser beam 18 is selectively moved (e.g., via the scanner 20) along a beam path to photoalter stromal tissue. For example, the focal spot 30 of the pulsed laser beam 18 is selectively directed along a predetermined length of the beam path in one reference area. The pulsed laser beam 18 is then redirected through another reference area, and the process of photoalteration is repeated. The sequence for directing the pulsed laser beam 18 through individually selected reference areas can be varied, and the extent of stromal tissue photoalteration, while the incising laser beam is so directed, can be varied. In one embodiment, the amount of photoalteration can be based on a refractive power map. In another embodiment, the sequence of reference areas that is followed during a customized procedure will depend on the particular objectives of the procedure.

To form the flap 41, the pulsed laser beam is scanned along the flap bed 43 and a sidecut 54 is made. The pulsed laser beams may be scanned using one or more scan patterns to one or more combinations of reference areas. One example of an ophthalmic scanning application is a laser in-situ keratectomy (LASIK) type procedure where a flap is cut from the cornea to establish extracorporeal access to the tissue that is to be photoaltered. Prior to or subsequent to scanning the flap bed 43, the sidecut 54 is created around a desired perimeter of the flap such that the ends of the sidecut terminate, without intersection, to leave an uncut segment 52. This uncut segment 52 serves as a hinge for the flap 41. The flap 41 is separated from the underlying stromal tissue by scanning the laser focal point across a flap bed 43. The perimeter of which is approximately defined by and slightly greater than the sidecut 54. Once this access has been achieved, photoalteration is completed, and the residual fragments of the photoaltered tissue are removed from the cornea. In another embodiment, intrastromal tissue may be photoaltered by the system 10 so as to create an isolated lenticle (e.g., not shown) of intrastromal tissue. The lenticle of tissue can then be removed from the cornea.

To scan the flap bed, the controller 22 selects a scan pattern that incises a peripheral portion 56 of the flap bed 43 while enhancing the healing capacity of flap 41 when reintegrated with the cornea 40. In one embodiment, the controller 22 directs the scanner 20 to scan the pulsed laser beam 18 along a first pattern in the peripheral portion 56 to produce a rougher separation surface (e.g., a "stickier" incision) of the stromal tissue (i.e., at the peripheral portion 56 as well as the corresponding portion of the flap 41). The scanner 20 scans the pulsed laser beam 18 along a second pattern in the remainder of the flap bed 43 to produce a smoother separation surface (e.g., a "cleaner" incision) of the stromal tissue (i.e., for the remainder of the flap bed 43 as well as the corresponding portion of the flap 41). For example, the first and second patterns may be differentiated by respective spot separations (i.e., between adjacent focal points of the pulsed laser beam 18 on the flap bed 43) such that the spot separation of the first pattern is generally greater than the spot separation of the second pattern. The rougher separation surface facilitates healing of the flap 41 with the cornea 40. Additionally, the rougher separation surface is desirable at the peripheral portion 56 where a flap edge 58 may be more susceptible to surface displacement or the like. A scan pattern associated with rougher separation surface is thus preferably used at the peripheral portion 56, although this scan pattern may be used at other locations of the flap bed 43.

Although, two different scan patterns are selected to scan the flap bed 43, multiple scan patterns may be used. Additionally, the controller 22 may select the different scan patterns based on other features that distinguish the tactile nature or relative smoothness of the resulting separation surfaces. The scan pattern producing the rougher separation surface may be used along all or a portion of the peripheral portion 56. The size and/or shape of the spots may also be varied and/or the relative accuracy of the scanning depth may be decreased (e.g., permitting greater variation of the scanning depth operating margin) to produce rougher separation surfaces.

In another embodiment, the sidecut 54 is preferably formed at an acute angle with respect to an optical axis, Z, associated with the optical axis of the cornea 40. This sidecut 54 produces a flap edge, such as the flap edge 58, with a tapered profile (e.g., radially decreasing in flap thickness from the anterior surface 46 of the cornea to a perimeter 60 of the flap bed 43). This tapered profile allows the flap edge 58 to be tucked into the stromal region 44 to enhance the biomechanical integrity of the flap 41 when reintegrated with the cornea 40. For example, the tucked flap edge 58 tends to resist surface tension that may be applied to the anterior surface 46 of the cornea. In combination with the use of scan patterns producing rougher separation surfaces of the stromal tissue on the flap bed, the biomechanical integrity is further enhanced.

Stromal tissue incisions via pulsed laser beams to produce rougher separation surface may also be used with the sidecut 54. For example, when forming the sidecut 54, the pulsed laser beam 18 may be scanned with a predetermined energy, spot size, and/or scan rate that produces a rougher sidecut. This rougher sidecut further enhances the biomechanical integrity of the flap 41 when reintegrated with the cornea 40 by increasing the healing capacity of the stromal tissue associated with this rougher sidecut. The rougher sidecut may be used to incise all or a portion of the flap edge 58.

Figure 4:
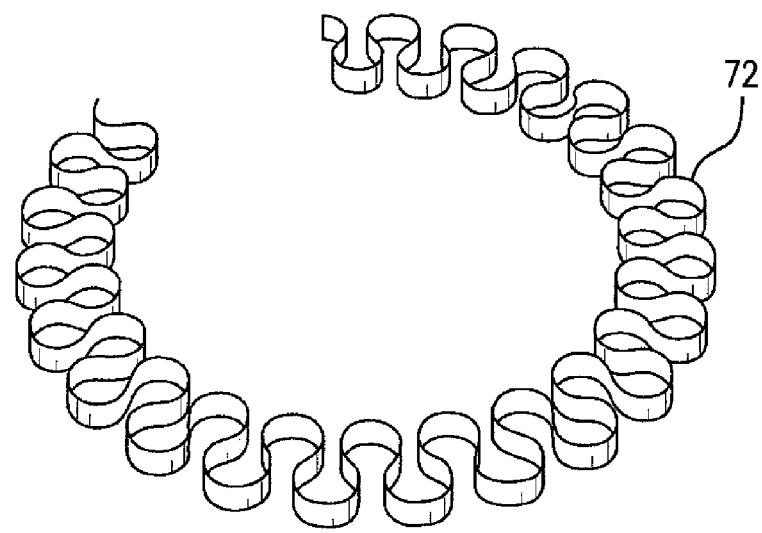
FIG. 4 is a perspective view of a flap edge in accordance with another embodiment.
Figure 5:
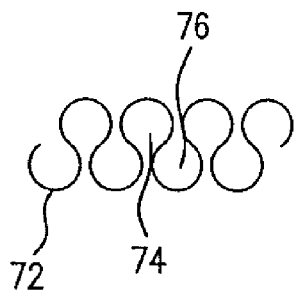
FIG. 5 is a top view of a portion of the flap edge shown in FIG. 4.

The biomechanical integrity of the flap may also be enhanced by incising a sidecut with an interlocking configuration. FIG. 4 is a perspective view of a flap edge 72 in accordance with one embodiment. FIG. 5 is a top view of a portion of the flap edge 72 shown in FIG. 4. Referring to FIGS. 1, 4, and 5, the flap edge 72 may be formed using the pulsed laser beam 18 to incise a sidecut with substantially circular eyelets 74 in a material. The eyelets 74 of the flap edge 72 interlock with corresponding substantially circular eyelets 76 of the remaining material. Although not shown, the flap edge 72 may also be configured with an interlocking profile. For example, the flap edge 72 may have a tapered profile, such the flap 41 shown in FIGS. 2 and 3. The flap edge may also be configured with other interlocking profiles, such as a top-hat shaped profile, a zig-zag profile, or the like. These interlocking profiles effectively enhance the biomechanical integrity of the flap along the z-axis or an axis substantially perpendicular to the surface of the cornea.

Figure 6:
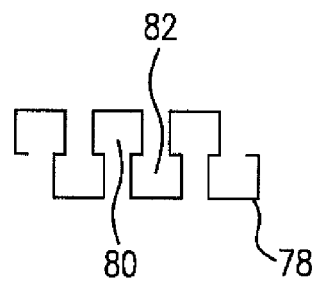
FIG. 6 is a top view of a flap edge in accordance with another embodiment.
Figure 7:
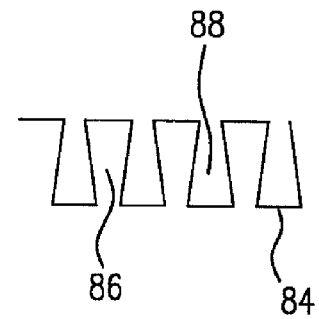
FIG. 7 is a top view of a flap edge in accordance with another embodiment.

Other interlocking configurations may be used to enhance the biomechanical integrity of the flap. FIG. 6 is a top view of a flap edge 78 in accordance with another embodiment. Referring to FIGS. 1 and 6, the flap edge 78 may also be formed using the pulsed laser beam 18 to incise a sidecut with substantially rectangular eyelets 80 in the material. The eyelets 80 of the flap edge 78 interlock with corresponding substantially rectangular eyelets 82 of the remaining material. FIG. 7 is a top view of a flap edge 84 in accordance with another embodiment. Referring to FIGS. 1 and 7, the flap edge 84 may also be formed using the pulsed laser beam 18 to incise a sidecut with substantially triangular eyelets 86 in the material. The eyelets 86 of the flap edge 84 interlock with corresponding substantially triangular eyelets 88 of the remaining material.

In one application, corneal tissue may be incised by scanning (e.g., using the scanner 20 in response to the controller 22) the pulsed laser beam 18 along a pattern having periodic alternating eyelets (e.g., the substantially circular eyelets 74 and 76, the substantially rectangular eyelets 80 and 82, the substantially triangular eyelets 86 and 88, or the like) to form a sidecut in the corneal tissue. The frequency and type of eyelets may be varied, although at least two substantially similar mating eyelets are preferably incised in sequence. This sidecut is thus created around a desired perimeter of the flap such that the ends of the sidecut terminate, without intersection, to leave an uncut segment. This uncut segment serves as a hinge for the flap.

Figure 8:
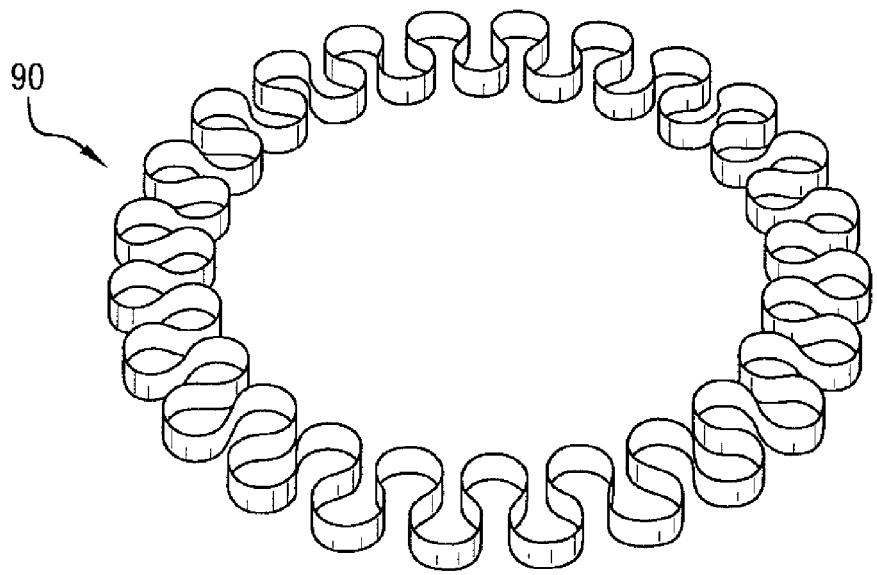
FIG. 8 is a top view of a corneal implant edge in accordance with another embodiment.

Although described in the context of corneal flaps, the interlocking configurations shown in FIGS. 4-7 may be used for a variety of corneal tissue applications. FIG. 8 is a top view of a corneal implant edge 90 in accordance with one embodiment. The corneal implant edge 90 is preferably incised with an interlocking configuration that substantially matches the edge of the recipient corneal tissue. These interlocking configurations facilitate positioning of corneal transplant implants of LASIK flaps. Additionally, the interlocking configurations secure the flap or implant against separation, translation (e.g., slippage), and rotation. Although the corneal implant edge 90 has one type of interlocking configuration, the frequency and type of interlocking portions may be varied. For example, incising at least two different interlocking portions, such as at least two different interlocking eyelets, facilitates orientation of the corneal implant edge 90 with respect to the recipient corneal tissue. The interlocking configurations also have an increased surface area in comparison with circular or oval incisions, which facilitates higher mechanical strengths after healing of the corneal tissue. While multiple interlocking portions (e.g., eyelets) are described in the flap edges 72, 78, and 84 and the corneal implant edge 90, the number of interlocking portions may be varied (e.g., one or more).

U.S. Pat. No. 6,805,694 and U.S. Pat. Publication No. 2006/0155265, which are incorporated herein, describe patterned profiles on sidecut edges for increasing flap stability. These patterned profiles stabilize the flap from shear tension and motion perpendicular to the plane of the flap bed. In contrast, the patterns of the system 10 (e.g., the roughened separation surfaces and interlocking configurations illustrated in FIGS. 4-8) stabilize the incision primarily against shear and stretching tension within the flap bed. For example, these patterns used in the system 10 reduce the chance of induced ectasia, which is an abnormal bulging of the corneal surface. In full-thickness corneal transplant applications, the interlocking sidecut patterns provide a unique benefit. Corneal tissue encounters continuous stretching tension from intraocular pressure, and there is no uncut tissue with full-thickness corneal transplant applications, such as the flap bed in LASIK procedure, that may support this tension. In conventional procedures, sutures initially support the stretching tension, and after suture removal, the wound line supports the tension in the tissue. Using the patterns with the system 10, additional support is provided to support the stretching tension.

Figure 9:
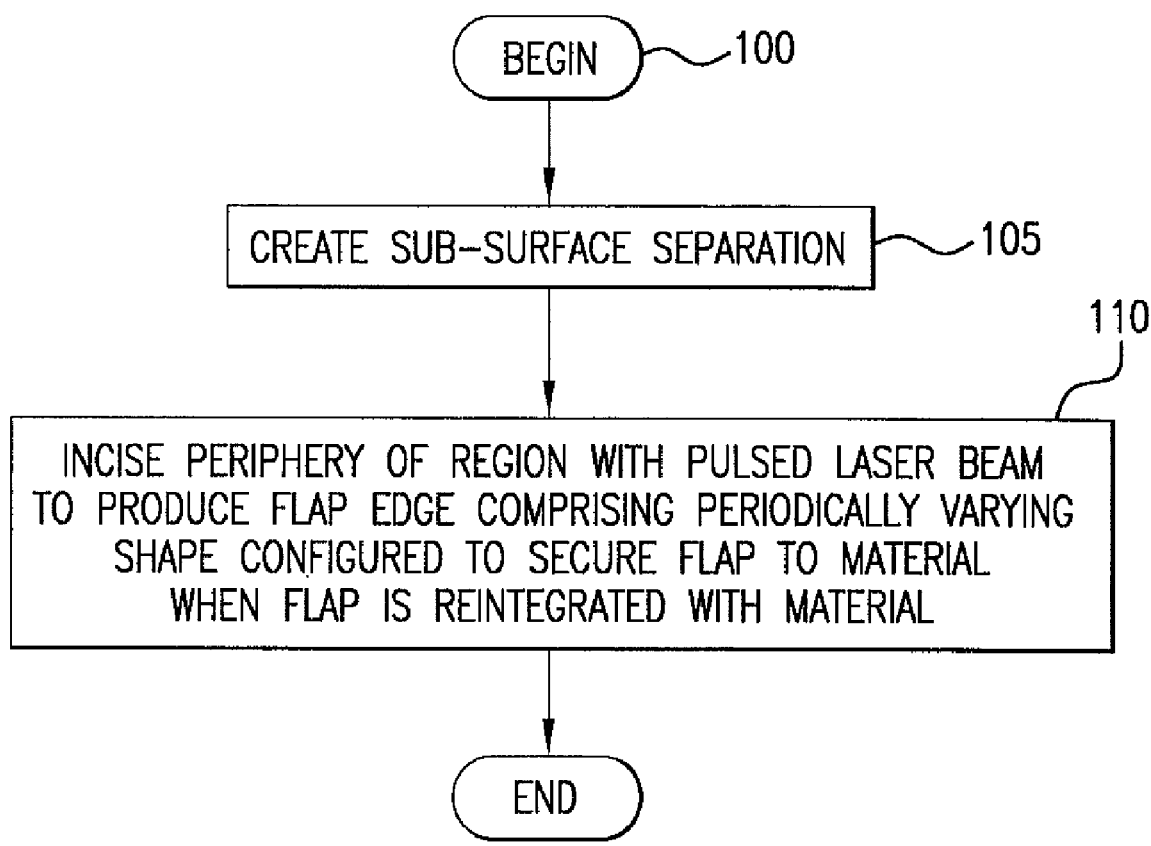
FIG. 9 is a flow diagram of a method for incising a portion of a material in accordance with one embodiment.

FIG. 9 is a flow diagram of a method 100 for incising a piece of a material in accordance with one embodiment. A sub-surface separation is created in a desired region of the material, as indicated at step 105. In one embodiment, a pulsed laser beam is scanned along a scan bed of the material with a single pattern, and the scan bed is below the surface of the material. For example, referring to FIGS. 1, 3, and 9, the pulsed laser beam 18 may be scanned (e.g., via the scanner 20 in response to the controller 22) along the flap bed 43.

A periphery of the region is incised with a pulsed laser beam to produce an edge of the flap, as indicated at step 110. In one embodiment, the edge includes a periodically varying shape to secure the flap to the material when the flap is reintegrated with the material. In one embodiment, the region has a circumference, and the pulsed laser beam is directed along the circumference in a periodically varying pattern to produce the flap edge. For example, referring to FIGS. 1 and 4-7, the pulsed laser beam 18 may be scanned with a periodically varying pattern to produce one of the flap edges 72, 78, and 84. In another embodiment, a plurality of periodic interlocking portions (e.g., the substantially circular eyelets 74 and 76, the substantially rectangular eyelets 80 and 82, the substantially triangular eyelets 86 and 88, or the like) is incised along the periphery of the region. In this embodiment, the material is incised to produce a first plurality of interlocking portions (e.g., the eyelets 74, 80, 86, or the like) and a second plurality of interlocking portions (e.g., the eyelets 76, 82, 88, or the like) with the first plurality of interlocking portions in a staggered relation with respect to the second plurality of interlocking portions when the flap is reintegrated with the material.

The surface may be separated into a flap portion (e.g., the flap 41) and a remainder portion (e.g., the flap bed 43). The periodically varying pattern adds a tensile strength to the surface of the material when the flap portion is reintegrated with the remainder portion.

In another embodiment, the flap bed has a first area and a second area contiguous with the first area, and the second area is less smooth than the first area. For example, the pulsed laser beam 18 is scanned with a first pattern along the peripheral portion 56 of the flap bed 43, and the pulsed laser beam 18 is scanned with a second pattern along the remainder of the flap bed 43. The second pattern has a spot separation that is less than the spot separation of the first pattern. The pulsed laser beam 18 is scanned along the second area (e.g., the peripheral portion 56) with a pattern configured to assist healing of the flap 41 with the flap bed 43 when the flap 41 is reintegrated with the cornea 40. The flap edge 58 is formed from the peripheral portion 56 of the flap bed 43 and tapers from the anterior surface 46 to the flap bed 43 to form a wedge-shape. A sidecut 54 is formed in the cornea 40 from the anterior surface 46 to the flap bed 43 in the peripheral portion 45 of the flap bed 43. At least a portion of this sidecut 54 is less smooth than the first area (e.g., the remainder of the flap bed 43). The sidecut 54 is thus configured to assist healing of the flap edge 58 with the cornea 40 when the flap 41 is reintegrated with the cornea 40.

Thus, systems and methods of preparing a flap of a material with a pulsed laser beam are disclosed that improve the biomechanical integrity of material with the flap reintegrated therewith. In one embodiment, these systems and methods pro-actively enhance the healing of corneal flaps or corneal transplants. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A method of incising a piece of a material, the material having a surface, the method comprising the steps of:
   creating a sub-surface separation in a region of the material, the sub-surface separation comprising a bed in the material, the bed comprising a first surface area and a second surface area, the first surface area at least partially surrounding the second surface area, wherein the step of creating comprises;
   scanning the pulsed laser beam with a first pattern of beam spots along the first surface area, the first pattern having a first spot separation; and
   scanning the pulsed laser beam with a second pattern of beam spots along the second surface area, the second pattern having a second spot separation less than the first spot separation, the first surface area being less smooth than the second surface area based on the spot separations; and
   incising a periphery of the region with a pulsed laser beam to produce an edge of the piece, the edge comprising a periodically varying shape configured to secure the piece to the material when the piece is reintegrated with the material.

2. The method of claim 1, further comprising separating the surface into a flap and a remainder, the periodically varying pattern being further configured to add a tensile strength to the surface of the material when the flap is reintegrated with the remainder.

3. The method of claim 1, wherein the piece is a flap, and wherein the region has a circumference, and wherein the step of incising comprises directing the pulsed laser beam along the circumference in a periodically varying pattern to produce the edge of the flap.

4. The method of claim 1, wherein the step of incising comprises incising a plurality of periodic interlocking portions along the periphery of the region.

5. The method of claim 4, wherein the step of incising a plurality of periodic interlocking portions comprises incising the material to produce a first plurality of interlocking portions and a second plurality of interlocking portions, the first plurality of interlocking portions in a staggered relation with respect to the second plurality of interlocking portions when the piece is reintegrated with the material.

6. A method of claim 1, wherein the material comprises a donor tissue and a recipient tissue, and wherein the step of incising comprises incising a plurality of periodic interlocking portions in the donor tissue and the recipient tissue to create full thickness incisions for corneal transplant.

7. The method of claim 1, wherein the step of creating comprises scanning the pulsed laser beam along a scan bed with a single pattern, the scan bed below the surface of the material.

8. The method of claim 1, wherein the step of creating comprises scanning the pulsed laser beam along a scan bed with at least two different scan patterns, the scan bed below the surface of the material.

9. A system for incising a piece of a cornea having a surface and a bed, the bed comprising a first sub-surface area and a second sub-surface area at least partially surrounded by the first sub-surface area, the system comprising:
   a laser operable to produce a pulsed laser beam;
   a controller operable to produce a control signal; and a scanner coupled to the controller and operable in response to the control signal to:
create a sub-surface separation in a region of the cornea with the pulsed laser beam by:
scanning a first pattern of beam spots along the first sub-surface area with the pulsed laser beam, the first pattern having a first spot separation; and
scanning a second pattern of beam spots along the second sub-surface area with the pulsed laser beam, the second pattern having a second spot separation less than the first spot separation, the first pattern being less smooth than the second pattern based on the first and second spot separations; and
incise a periphery of the region with the pulsed laser beam to produce an edge of the piece, the edge comprising a periodically varying shape configured to secure the piece to the cornea when the piece is reintegrated with the cornea.

10. The system of claim 9, wherein the control signal further directs the scanner to incise the surface with the pulsed laser beam into a flap portion and a remainder portion, the profile of the edge being further configured to add a tensile strength to the surface of the cornea when the flap portion is reintegrated with the remainder portion.

11. The system of claim 9, wherein the cornea has a scan bed below the surface of the cornea, and wherein a profile of the edge tapers from the surface to the scan bed.

12. The system of claim 9, wherein the region has a circumference, and wherein the control signal further directs the scanner to scan a pattern with the pulsed laser beam to produce the edge of the piece, the pattern periodically varying with respect to the circumference, the profile of the edge having a periodically varying shape corresponding with the periodically varying pattern.

13. The system of claim 9, wherein the cornea is selected from at least one of a donor cornea and a recipient cornea, and wherein the control signal further directs the scanner to incise the periphery of the region with the pulsed laser beam to produce a full-thickness incision having the edge.

14. The system of claim 9, wherein the control signal further directs the scanner to incise the cornea with the pulsed laser beam to produce a first plurality of interlocking portions and a second plurality of interlocking portions, the first plurality of interlocking portions in a staggered relation with respect to the second plurality of interlocking portions when the piece is reintegrated with the cornea.

* * * * *